United States Patent [19]
Barker et al.

[11] Patent Number: 5,182,083
[45] Date of Patent: Jan. 26, 1993

[54] SAMPLE WHEEL FOR CHEMISTRY ANALYZERS

[75] Inventors: Stephen F. Barker, La Mirada; Samuel G. Ricchio, Fullerton; Glenn A. Benton, Hesperia; Delbert D. Jackson, Placentia, all of Calif.

[73] Assignee: Beckman Instruments, Inc., Fullerton, Calif.

[21] Appl. No.: 322,802

[22] Filed: Mar. 13, 1989

[51] Int. Cl.$^5$ .................... B65G 47/00; B65G 47/244
[52] U.S. Cl. ........................... 422/63; 422/64; 422/65; 141/168; 141/170; 198/345.2
[58] Field of Search .................. 422/63, 64, 65, 67; 141/130, 170, 168; 73/864.23, 864.24; 198/345.2

[56] References Cited

U.S. PATENT DOCUMENTS

| | | | |
|---|---|---|---|
| 3,945,412 | 3/1976 | Forsstrom | 422/64 |
| 4,099,460 | 7/1978 | Bubley et al. | 198/345.2 |
| 4,166,094 | 8/1979 | Froehlich et al. | 422/64 |
| 4,363,245 | 12/1982 | Schmid | 73/864.22 |
| 4,836,038 | 6/1989 | Baldwyn | 422/64 |

FOREIGN PATENT DOCUMENTS 2361195 3/1978 France .
2190889 12/1987 United Kingdom .

*Primary Examiner*—Robert J. Warden
*Assistant Examiner*—Krisanne M. Thornton
*Attorney, Agent, or Firm*—William H. May; Gary T. Hampson; Charles Berman

[57] ABSTRACT

An automatic chemistry analyzer includes sample cups circumferentially located on a sample wheel. Means moves the sample cups rotationally under cycloidal action to and away from a target location where a probe operates vertically in relation to the sample cups and an injection cell. The motion is effected by a cam operating with a cam follower formed by lobes circumferentially located about a drive wheel which houses the sample wheel or carousel.

22 Claims, 3 Drawing Sheets

SAMPLE WHEEL FOR CHEMISTRY ANALYZERS

RELATED APPLICATIONS

This invention relates to the inventions and disclosures which are the subject of application Ser. Nos.:
07/322,814 filed Mar. 13, 1989
07/322,810 filed Mar. 13, 1989
07/322,811 filed Mar. 13, 1989
07/322,812 filed Mar. 13, 1989
07/322,813 filed Mar. 13, 1989
07/322,807 filed Mar. 13, 1989
All these applications are filed contemporaneously with the present application and the contents of them all are incorporated by reference herein.

BACKGROUND

This invention relates to the field of automatic analytical instruments, and, more particularly, the invention is concerned with instruments for automatic clinical chemistry systems using sample carousels and sample handling systems.

Different clinical analyzers for automatic analyzers are known. One particular kind uses a plurality of individual analysis modules having open reaction or sample cups. An automated sample probe withdraws a sample volume from samples in sample cups carried on a carousel. Selected volumes of the sample are distributed to analysis modules in accordance with tests selected by the instrument operator.

A different kind of analyzer uses a flow cell through which diluent flows together with fluid samples for determination of electrolytes in the fluid sample. Usually, four electrolytes, namely, sodium, potassium, chloride an $CO_2$ are determined in the flow cell. In such analyzers, a sample pick-up probe extends vertically through a shear valve to aspirate the fluid sample from a sample cup aligned with the probe. The tip of the probe is withdrawn into a shear valve and the lower portion of the valve closes. Diluent from a diluent source flows into the valve, is mixed with the sample from the probe and flows to a flow analysis module.

Each of these different kinds of analyzers have their unique advantages in the analysis of fluid samples. For instance, the first analyzer enables the parallel analysis of samples using incompatible reagents that could not be used in a flow cell analysis module. On the other hand, a flow cell analyzer provides simplified fluid handling and minimizing reagent consumption.

The present invention is particularly directed to the flow cell analyzer and systems for improving the movement and operation of various components, particularly, the sample carousel or wheel, and the sample-handling system.

SUMMARY

The present invention solves the problems posed in the prior art by providing a simplified system for movement of a sample wheel and the sample handling.

According to the invention, an automatic clinical chemistry apparatus comprises discrete elements located in a row associated with a body. Means are provided for progressively moving the elements towards and from a target location. Motor means rotates a cam which engages a follower on the body to cause the follower to move the body laterally and transversely towards the target location during a first predetermined portion of travel of the cam. A second predetermined portion of travel of the cam causes lateral and transverse motion away from the target location. In a third predetermined portion of travel of the cam, the body remains in a position away from the target location. The motion of the body is effectively cycloidal and is generated by a single motor.

Preferably, the body is a drive wheel and the elements are receptacles associated with the drive wheel, the receptacles being sample containers or cups for sample fluids. The target location is a position adjacent an injection cell where there are means for transferring the contents of the elements to the injection cell. The elements are preferably contained in a row in a sample wheel housed with the drive wheel.

The outer periphery of the drive wheel includes lobes for engagement with the cam, the lobes acting as the cam follower.

The drive wheel includes a plurality of notches wherein locking of the wheel against movement during the third predetermined portion of travel or the cam is effected. This is achieved by engaging an extension of the drive shaft of a motor in a selected notch.

Other features of the invention will become apparent from the following detailed description and drawings.

DESCRIPTION

Figure 1:
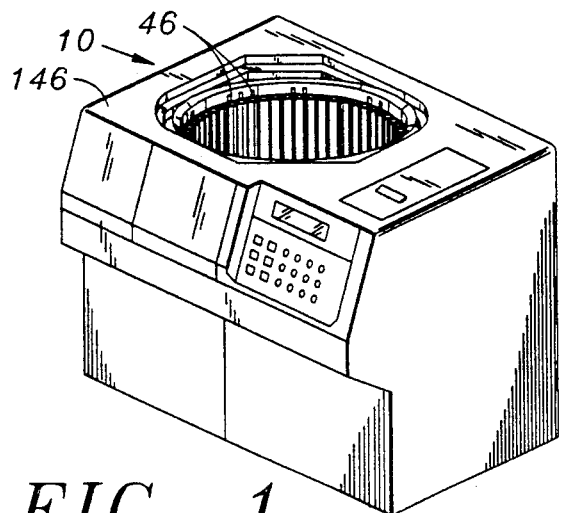
FIG. 1 is a perspective view of an automatic clinical chemistry analyzer illustrating a drive wheel and a sample wheel mounted in the top face of the analyzer.
Figure 3:
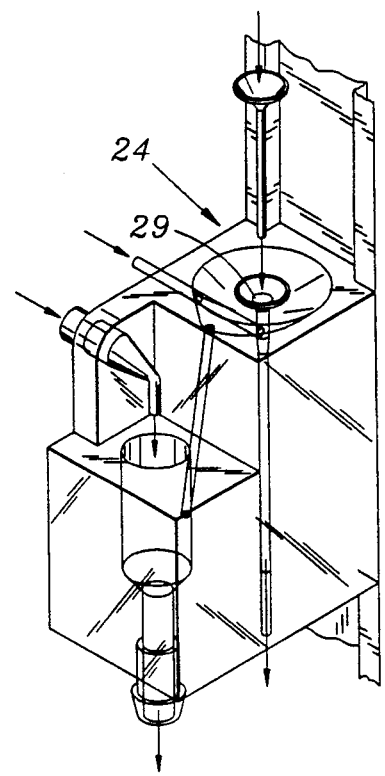
FIG. 3 is a perspective view of an injection cell illustrating a probe in relation to the bore of the cell.
Figure 2:
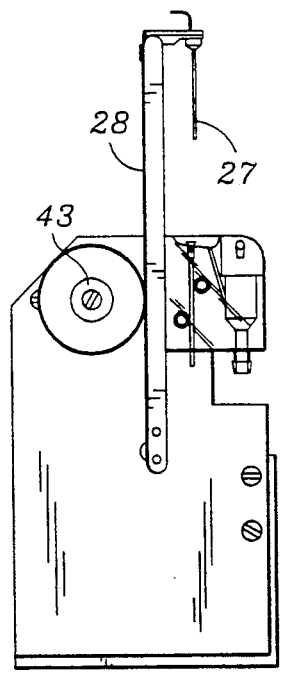
FIG. 2 is a side view of a crane mounting a probe, the probe being operative between sample tubes or cups in the sample wheel and an injection cell in the analyzer.

An automatic clinical chemistry analyzer 10 includes discrete elements 11 located in a row on a body 12 which is a sample wheel or carousel. The discrete elements are sample cups or containers 11 mounted in a sample wheel 12 which is in turn mounted in a drive wheel 13.

Means for progressively moving the elements 11 towards and from a target location 14 includes a motor means 15 mounted below a plate 16. The motor means 15 rotates a cam 17 and a bearing surface 18 of the cam 17 engages a follower surface 19 on the drive wheel 13. Engagement of the bearing surface 18 with the follower surface 19 moves the body 13 laterally and transversely towards the target location 14 during a first predetermined portion of travel of the cam 17. During a second predetermined portion of travel of the cam 17, the drive wheel 13 is laterally and transversely moved away from the target location 14. The drive wheel 13 remains in a position removed from the target location 14 during a third predetermined portion of travel of the cam 17.

Figure 11:
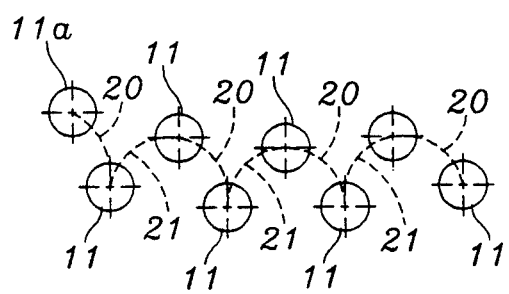
FIG. 11 is a diagrammatic plan view illustrating the cycloidal motion of reaction cups in the sample wheel contained in the drive wheel.

During this first, second and third predetermined portions of travel, the sample cups 11 follow a travel path which is respectively a first quarter circular path 20 and a second quarter circular path 21. The two quarter circular paths 20 and 21 constitute a semi-circular path. During the third predetermined portion of travel of the cam 17, the cups 11 remain stationary. The cam 17 travels the remainder of the semi-circular path thereby to close the circle with the quarter circular paths 20 and 21. This effects a travel path for the cups 11 which is cycloidal. This is indicated in FIG. 11. The cam 17 transcribes a circular path under driven action from the motor 15 about the axis of shaft 22 which extends from a gear box 23 connected with and mounted downstream the motor 15.

The target location 14 is located adjacent an injection cell 24 which is mounted below the aperture 25 in the base 26 at the top of the clinical analyzer 10. A probe 27 is mounted on a crane 28 to transfer fluid from the sample cups 11 to the inlet port 29 of the injection cell 24. The crane 28 is selectively movable between the sample cups 11 and the injection cell 24.

The outer periphery 19 of the drive wheel 13 includes lobes 30 which act as a cam follower. The lobes have a generally sinusoidal track around the circumference of the drive wheel 13. The outer periphery of the lobes 30 has a greater radius 31 than the valleys 32 of the lobes 30.

Pin means 33 at the extremities of a pair of restraining levers 34 acts to urge the drive wheel 13 towards the motor 15. The levers 34 are mounted about pivots 35 and a spring connection 36 fixed to pins 37 acts to draw the drive wheel 13 towards the rotor 15. Thus, when the wheel 13 is forced away from the motor under the action of the cam 17, the force from pins 33 urge and returns the drive wheel 13 in the direction of the motor 15. The pins 37 engage the inner surface 38 of the drive wheel 13. The drive wheel 13 reacts with the cam 17 and the counterforce pins 33, to effect the cycloidal action.

The drive wheel 13 rests on a base 39 and is constrained to substantially rotational movement about an axis 200 on the base 39. Such rotational movement is constituted by lateral and transverse motion as defined in the first predetermined portion of travel and the second predetermined portion of travel. The base 39 includes side walls 40, 41 and 42 for facilitating constraint of the wheel 13 from lateral movement beyond the rotational movement. Effectively, side walls 41 and 42 constrain the lateral movement. Hence, the side wall 40, together with the pins 33, can act to limit movement away from the motor 15.

A cycloidal motion is accomplished on the sample wheel 12 which is housed in the drive wheel 13. In this manner, the sample receptacles 11 simultaneously transverse a cycloidal path. The receptacles or cups 11, move laterally and transversely towards and away from the target location 14 in this cycloidal fashion.

A single motive means 15 effects both rotational movement of the drive wheel 13 and sample wheel 12 and also movement towards and away from the target location 14. The combination of the lateral and transverse motions create the requisite rotational cycloidal movement of the drive wheel 13. The single motive means 15 achieves this. A single crane motor 43 operative with crane 28, causes vertical upwards and downwards motion of the crane 28. The requisite rotational cycloidal motion and the vertical motion of the crane 28 is thereby accomplished with only two motors, namely, motors 15 and 43.

Figure 8:
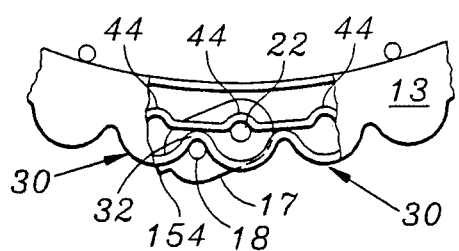
FIG. 8 is a partial plan view, with parts broken away, illustrating the relationship of the cam with the drive wheel, the cam being located in a valley between adjacent lobes of the drive wheel.

In a first exemplary position of the cycle, there is illustrated in FIG. 8 the cam 17 with the bearing surface 18 and the valley 32 of lobe 30 of the drive wheel 13. The drive motor shaft extension 22 from the gear box 23 is located in a notch 44 which are selectively arranged in predetermined locations about the drive wheel 13. The notches 44 are spaced circumferentially from each other and inwardly of the lobes 30. Rotation of the cam 17 through one rotation advances the drive wheel 13 through one increment and the sample wheel 12 is similarly moved through one increment. Movement of one increment would progressively locate adjacent cups 11 in the target location 14.

Figure 10:
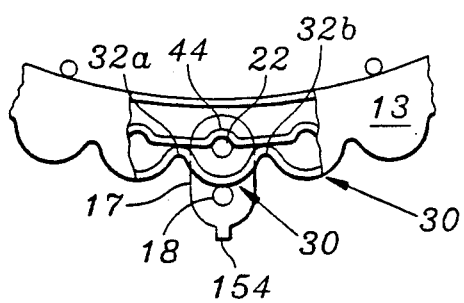
FIG. 10 is a partial plan view, with parts broken away, of the drive wheel in relationship with the cam, and showing the cam located at the peak of a lobe in the drive wheel, and a shaft extension from a drive motor located in a locking notch on the drive wheel. The position in the cycle of motion is the same as depicted in FIG. 7, namely the peak position between the locations illustrated in FIGS. 8 and 9.

During the half revolution of the cam 17, the bearing surface 18 tracks from the valley 32a illustrated in FIGS. 8 and 10 to the valley 32b following the peak 30 of the follower 31. The extension of shaft 22 is anchored in the notch 44 during this movement, and the drive wheel 13 is thus stationary. This movement of the cam 17 equates to the closing a semi-circle, namely, during the third predetermined travel path.

Figure 9:
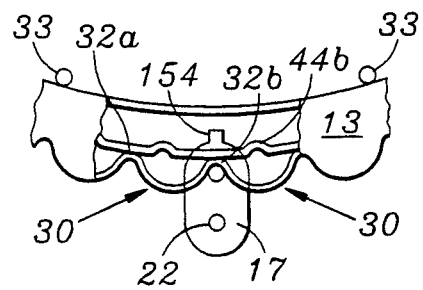
FIG. 9 is a partial plan view, with parts broken away, illustrating the cam relationship with the cam in a valley adjacent the valley of FIG. 8.

When the bearing surface 18 engages the valley 32b, as illustrated in FIG. 9, the drive wheel 13 is pushed forwardly, transversely and laterally towards the target location 14. This movement is away from the motor 15. This would correspond to the first predetermined portion of travel 20 of the cups 11. The notch 44 is disengaged. As the travel of the cam 17 continues through the next quarter-circle corresponding to the travel path 21, the bearing surface 18 moves the valley 32b in a transverse and lateral direction away from the target location 14. This movement continues until the shaft extension 22 engages in the notch 44b illustrated in FIG. 9. In this action, the element is passing through the second predetermined travel path. The motion of the cups 11 is towards the motor 15 under the action of the restraining or counterforce pins 33.

Thereafter, the cycle, illustrated progressively in FIG. 8 to FIG. 10 to FIG. 9 is repeated. The counterforce pins 33 continue to urge the drive wheel 13 towards the cam 17 and motor 15. During this time, the cups 11 traverse the cycloidal path illustrated in FIG. 11. Each cup 11 is, in turn, brought into the target location 14 for sampling by the probe 27 and when moved out of the target location 14, the probe 27 then enters the injection cell by descending through port 29.

The sample probe 27 is affixed to the crane mechanism 28 which holds the probe 27 in alignment with injection cell 24 mounted below the plate 26. This is located below the drive wheel 13 and sample wheel 12 mounted circumferentially about, within and on the drive wheel 13. The injection cell 24 is accessed through the aperture 25 at the target location 14. The probe 27 motion is vertical only.

The sample or receptacle cups or tubes 11 are mounted in discrete locations about the circumferential periphery of the sample wheel 12. The cups 11 are moved into position by the cycloidal motion of the sample wheel 12 as generated by the drive wheel 13. The sample wheel 12 follows a path indicated by lines 20 and 21 which brings the cups 11 from removed positions closer to the front face or motor 15 and away from the target location 14 to positions above the target location. When removed from the target location 14, the probe 27 descends into the port 29 of the injection cell 24. When located over the target location 14, the probe 27 enters the sample cup 11 which is located over the target location 14. The timing of the probe movement and action and the sample wheel 12 and drive wheel 13 action is under regulating and control of a microprocessor.

The cups 11 thereby effect the lateral and transverse motions which constitute the rotational motion of the sample wheel 12. The lateral motion is partly defined between the side walls 41 and 42 and the transverse motion is defined between the forward wall 45 and rear Wall 40 housing the drive wheel 13 and sample wheel 12. The vertical motion is provided by the crane 28 operating the probe 27. Accordingly, only two motors 15 and 43 are needed for effecting the requisite motion to cause travel of the sample wheel 13 rotationally and cycloidally. Vertical action removes samples from the cups 11 and dispenses them into the injection cell 24. This saves the complexity of three motive forces and improves reliability and reduces costs.

In FIG. 11, the positions between the respective semicircles constituted by quarter-circles 20 and 21 would correspond to the positions of the cups 11 where the sample is removed by the probe 27. In this position, the cam 17 operates through its third portion of travel. The cups 11 are stationary and removed from the target location 14, and the probe 27 aspirates into the injection cell 24.

Figure 4:
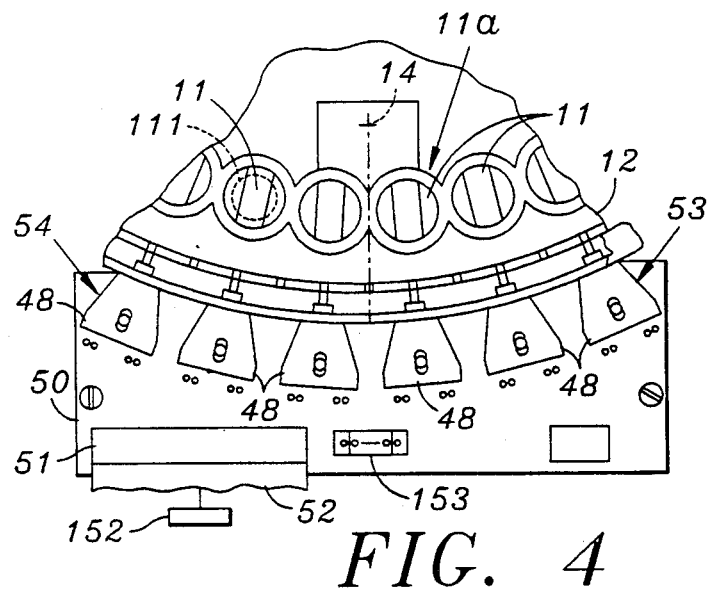
FIG. 4 is a partial plan view of the analyzer illustrating a part of a sample wheel, drive wheel and the sensors for coding the sample wheel located adjacent to the sample wheel and drive wheel.
Figure 5:
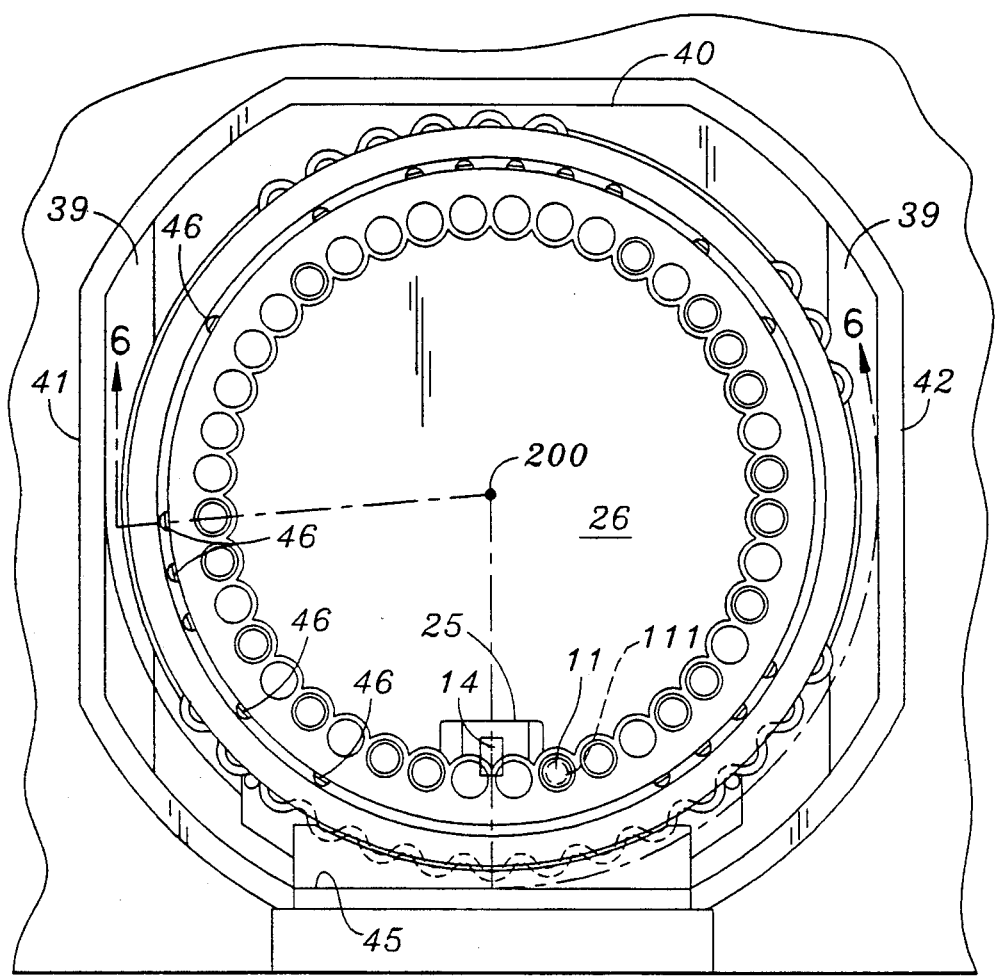
FIG. 5 is a plan view illustrating a portion of the top face of the chemical analyzer, and showing the drive wheel with the sample wheel located in the drive wheel.
Figure 6:
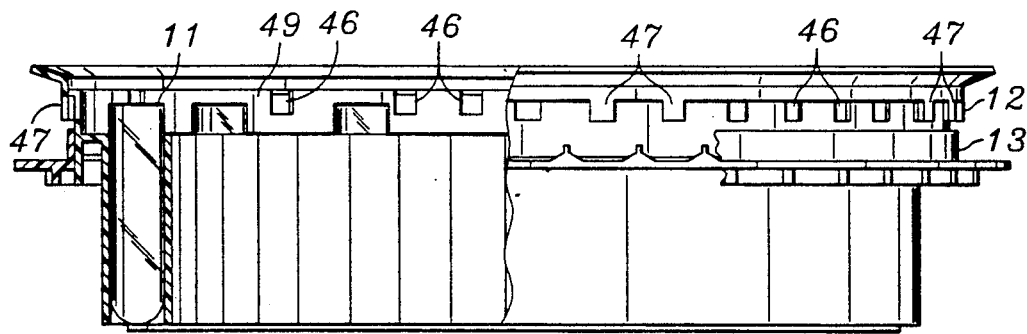
FIG. 6 is a side view of the drive wheel and sample wheel, partly in section, the section being along line 6—6 of FIG. 5.
Figure 7:
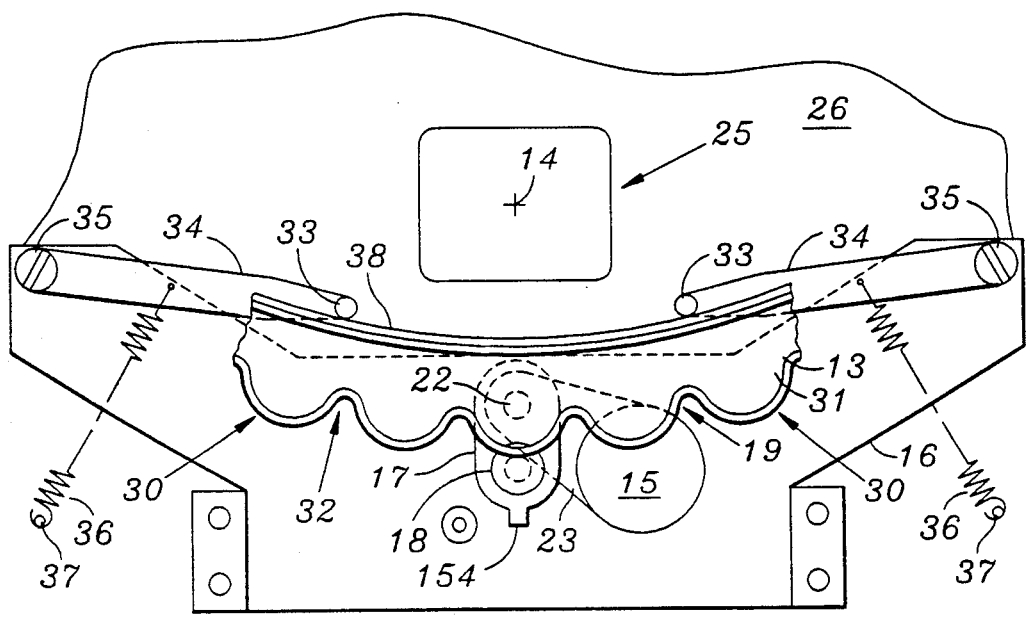
FIG. 7 is a partial plan view illustrating the relationship of the drive wheel with the cam and restraining pins, the cam being in a position at the peak of a lobe on the drive wheel.

In FIGS. 4 and 5, there is diagrammatically illustrated in two of the cups 11a circular sleeve adapter 11 which would be used within the periphery of the elements 11 to accommodate cups 11. In other cases, the sleeve adapters 111 could be used with smaller diameter tubes 11 which fit into the apertures about the sample wheel 13.

Discrete apertures 46 and periodically discretely spaced flags 47 are located about the sample wheel 12. The spaced apertures 46 and flags 47 are irregularly located in predetermined spaced manner about the outside circumference side wall 49 of the sample wheel 12.

Adjacent the front face 45 and below the top plate 146 of the analyzer are a series of six sensor units 48 spaced discretely and separately about the circumference of the sample wheel 12. The spacing is designed to correspond with the predetermined irregular spacing of apertures 46 and flags 47 on sample wheel 12. The sensor units 48 are of an optical nature and each include transmitter and receiver elements which depend on the reflectivity from the flags 47 of the sample wheel 12. Signal enhancement means is provided for the sensor units 48.

Effectively, maximum reflection is achieved by the flags 47 and minimum reflection is achieved due to the apertures 46. The sample tray wheel 12 thereby has molded as part of the side wall 49 the means for coding the location of the discrete sample cups 11. The relationship of the sample wheel 12 and drive wheel 13 is such that the sample wheel 12 is randomly located inside the drive wheel 13. The side wall 49 has at least that portion having the apertures 46 and flags 47 optically directed to the sensor unit 48. Thus the sample wheel 12 acts inherently to code for location of the cups 11 within the wheel 12. There are 40 sample cells 11 arranged around the circumference of the sample wheel 12 which can be coded and identified by the six sensor units 48.

The sensor units 48 are mounted on a circuit board 50 which interfaces at 51 with a cable 52 to a microprocessor 152. The microprocessor 152 can also constitute part of the control system for regulating the motion of the drive wheel 13, crane 28, and probe 27 operation with the cups 11 and injection cell 24.

As the sample tray 12 moves driven by the drive wheel 13, the apertures 46 and flags 47 move in a rotational fashion before the six sensor units 48. Periodic starting and stopping of the drive wheel 13 is effected.

A sensor 153 interacts with tab 154 on the cam 17 such that when the drive wheel 13 is in the position indicated in FIG. 10 reading of the apertures 46 and flags 47 can be effected. This would correspond to the position of the cups 11 removed from the target 14. In the positions illustrated in FIGS. 8 and 9 of the cam 17 the tab 154 is removed from the sensor 153. The sensors 48 do not read the apertures 46 and flags 47 in this position of the sample tray 12 and drive wheel 13.

A parallel decoding method is employed and a binary system is effective for coding. Reflectance is achieved when a flag 47 is before a sensor 48. This would be represented as a binary digit 0. Non-reflectance before a sensor 48 digit is indicative of an aperture 46 before the sensor 48. This is indicative of a digit 1. The sensor 53 is the most significant bit sensor and the sensor 54 is the least significant bit sensor.

The location target 14 is also illustrated in FIG. 4. As illustrated in FIG. 4, the sample wheel is in a position ready to move to the target location 14 where the probe 27 can remove the sample from sample cup 11A.

The binary positions can be represented by the following table:

| Position # Code | Binary Code (LSB-MSB) | Position # | Binary |
|---|---|---|---|
| 1 | 000000 | 21 | 000011 |
| 2 | 000001 | 22 | 000110 |
| 3 | 000010 | 23 | 001101 |
| 4 | 000101 | 24 | 011010 |
| 5 | 001010 | 25 | 110101 |
| 6 | 010101 | 26 | 101010 |
| 7 | 101011 | 27 | 010100 |
| 8 | 010111 | 28 | 101000 |
| 9 | 101111 | 29 | 010001 |
| 10 | 011111 | 30 | 100010 |
| 11 | 111110 | 31 | 000101 |
| 12 | 111101 | 32 | 001000 |
| 13 | 111010 | 33 | 010011 |
| 14 | 110100 | 34 | 100111 |
| 15 | 101001 | 35 | 001111 |

-continued

| Position # Code | Binary Code (LSB-MSB) | Position # | Binary |
| --- | --- | --- | --- |
| 16 | 010010 | 36 | 011110 |
| 17 | 100100 | 37 | 111100 |
| 18 | 001000 | 38 | 111000 |
| 19 | 010000 | 39 | 110000 |
| 20 | 100001 | 40 | 100000 |

The advantage of the coding system is that the necessary components are formed or mounted integrally with the sample wheel 12, which is rugged and durable. Protection against wear and chemicals is strong and effective, and there is no assembly nor the necessity to add stickers for coding. The system also provides for ease of application since the selected sample wheel 12 need simply be randomly located in the drive wheel 13 in any position. The apertures 46 and flags 47 are aligned with sensors 48 as required. The coding identification is straightforward and it is easy to index and identify which particular sample cup 11 relative to the code is to be accessed and analyzed.

With the above arrangement, the drive wheel 13 can be operated in either a clockwise or counterclockwise motion. It is always possible to identify easily the requisite sample cup 11 for analysis. By having two separate components, namely, the drive wheel 13 and sample wheel 12, the mechanism is easily operated. Different sample wheels 12 can be inserted with the drive wheel 13 as required with a minimum downtime.

Many other examples of the invention exist, each differing from the others in matters of detail only. For instance, although a drive wheel and sample wheel are illustrated the operation of the components with the cam could be with the reaction cups located in a linear, non-circular manner relative to the handling system. Similarly, the coding procedure for the sample wheel 12 can operate with configurations other than circular. The scope of the invention is to be determined sole by the appended claims.

We claim:

1. Apparatus comprising a body, discrete elements located in a row associated with the body, motive means for progressively moving the elements towards and from a target location relative to the body, the motive means including a motor and a cam, the motor rotating the cam, and a follower for engagement by the cam and for engagement with the body to cause the follower to move the body and associated elements respectively towards the target location during a first predetermined portion of travel of the cam, and away from the target location during the second predetermined portion of travel of the cam, wherein the cam and elements follow a predetermined travel path, the cam being rotatable about an axis and having means remote from the axis for engaging the follower such that the first predetermined portion of the travel path of the cam and elements is substantially a quarter-circular path, and the second predetermined portion of the travel path of the cam and elements is a quarter-circular path, the two quarter-circular paths constituting a semi-circular path for the cam and elements.

2. An apparatus as claimed in claim 1, wherein the cam engages the follower such that the travel path of the elements is cycloidal.

3. Apparatus as claimed in claim 1 wherein the follower is formed in the body, the body being a drive wheel, and wherein the elements are receptacles associated with the drive wheel.

4. Apparatus as claimed in claim 3 wherein the elements are contained in a sample wheel housed with the drive wheel.

5. Apparatus as claimed in claim 1 wherein the target location is a position adjacent an injection cell, and including means for transferring contents of the elements to the injection cell.

6. Apparatus as claimed in claim 5 wherein the transfer means is a crane selectively moveable between the receptacles and injection cell.

7. Apparatus as claimed in claim 1 wherein the row is contained about the circumference of a sample wheel, and the follower is formed about the circumference of a drive wheel, the drive wheel being the body.

8. Apparatus as claimed in claim 1 wherein the motive means is a motor mounted adjacent the body, and the cam is driven by a drive shaft of the motor.

9. Apparatus as claimed in claim 8 wherein the motive means includes gearing between the motor and the cam.

10. Apparatus as claimed in claim 7 wherein the motive means includes a motor located adjacent the circumference of the drive wheel and the cam is driven by the motor, the cam engaging an outer periphery of the wheel.

11. Apparatus as claimed in claim 10 wherein periphery of the drive wheel includes lobes for engagement with the cam, the lobes acting as the cam follower, and the lobes forming a generally sinusoidal path around the circumference of the wheel.

12. Apparatus as claimed in claim 11 including a plurality of notches in the drive wheel and wherein locking of the ring against movement during the third predetermined portion of travel of the cam is effected by engagement of an extension of the drive shaft of the motor in a selected notch in the wheel.

13. Apparatus as claimed in claim 12 including means for urging the drive wheel towards the motor.

14. Apparatus as claimed in claim 13 wherein the means includes spring biased levers, the levers having pin protrusions at their extremities and being adapted to engage the inner surface of the drive wheel and bias the drive wheel towards the motor.

15. Apparatus as claimed in claim 10 wherein the drive wheel rests on a base, and the drive wheel is constrained to substantially rotational movement on the base, such movement being constituted by the lateral and transverse motion defined in the first predetermined portion of travel of the elements and the second predetermined portion of travel of the elements.

16. Apparatus as claimed in claim 15 wherein the base includes side walls for facilitating constraint of the wheel from lateral movement beyond the rotational movement.

17. Apparatus comprising a body, discrete elements located along a line in a row associated with a body, motive means for progressively moving the line of elements towards and from a target location relative to the body, the motive means including a motor and a cam, the motor rotating the cam, and a follower for engagement by the cam and engagement with the body to cause the follower to move the body and associated line of elements respectively towards the target location during a first predetermined portion of travel of the cam, and to move the line of elements away from the target location during the second predetermined portion of travel of the cam, wherein the cam and elements follow a predetermined travel path, the cam being rotatable about an axis and having means remote from the axis for engaging the follower such that the first predetermined portion of the travel path of the cam and elements is substantially a quarter-circular path, and the second predetermined portion of the travel path of the cam and elements is a quarter-circular path, the two quarter-circular paths constituting a semi-circular path for the cam and elements.

18. Apparatus comprising a body, discrete elements located along a line a row associated with a body, motive means for progressively moving the line of elements towards and from a target location relative to the body, the motive means including a motor and a cam, the motor rotating the cam, and a follower for engagement by the cam and engagement with the body to cause the follower to move the body and associated line of elements respectively towards the target location during a first predetermined portion of travel of the cam, and to move the line of elements away from the target location during the second predetermined portion of travel of the cam, wherein the cam engages the follower such that the travel path of the elements is cycloidal.

19. Apparatus as claimed in claim 17 wherein the follower is formed in the body, the body being a drive wheel, and wherein the elements are receptacles associated with the drive wheel.

20. Apparatus as claimed in claim 19 wherein the elements are contained in a sample wheel housed with the drive wheel.

21. Apparatus as claimed in claim 17 wherein the target location is a position adjacent an injection cell, and including mans for transferring contents of the elements to the injection cell.

22. Apparatus as claimed in claim 17 wherein the row is contained about the circumference of a sample wheel, and the follower is formed about the circumference of a drive wheel, the drive wheel being the body.

* * * * *

UNITED STATES PATENT AND TRADEMARK OFFICE
CERTIFICATE OF CORRECTION

PATENT NO.  : 5,182,083
DATED       : January 26, 1993
INVENTOR(S) : Barker et al It is certified that error appears in the above-indentified patent and that said Letters Patent is hereby corrected as shown below:

Col. 5, line 51 reads "adapter 11" should read --adapter 111--.

Col. 6, line 48 reads "sample wheel is" should read --sample wheel 12 is--

Col. 9, line 12 reads "located along a line a row associated" should read --located in a row associated--.

Signed and Sealed this

Twelfth Day of April, 1994

Attest:

BRUCE LEHMAN

Attesting Officer

Commissioner of Patents and Trademarks